United States Patent
Lai et al.

(10) Patent No.: US 7,972,134 B2
(45) Date of Patent: Jul. 5, 2011

(54) RESPONSE SURFACES FOR ORTHODONTIC TREATMENT PLANNING

(75) Inventors: Ming-Lai Lai, Arcadia, CA (US);
Andrew W. Chen, Woodbury, MN (US);
Jennifer L. Trice, Eagan, MN (US);
Gopal B. Haregoppa, Woodbury, MN (US)

(73) Assignee: 3M Innovative Properties Company, Saint Paul, MN (US)

( * ) Notice: Subject to any disclaimer, the term of this patent is extended or adjusted under 35 U.S.C. 154(b) by 413 days.

(21) Appl. No.: 11/096,785

(22) Filed: Apr. 1, 2005

(65) Prior Publication Data

US 2006/0223023 A1    Oct. 5, 2006

(51) Int. Cl.
*A61C 3/00* (2006.01)

(52) U.S. Cl. .......................................... 433/24

(58) Field of Classification Search ................... 433/24
See application file for complete search history.

(56) References Cited

U.S. PATENT DOCUMENTS

| | | |
|---|---|---|
| 4,975,052 A | 12/1990 | Spencer et al. |
| 5,131,844 A | 7/1992 | Marinaccio et al. |
| 5,431,562 A * | 7/1995 | Andreiko et al. ............... 433/24 |
| 5,454,717 A | 10/1995 | Andreiko |
| 5,533,895 A | 7/1996 | Andreiko et al. |
| 5,616,866 A | 4/1997 | Murakami |
| 5,975,893 A | 11/1999 | Chishti et al. |
| 6,080,199 A | 6/2000 | Umeyama et al. |
| 6,120,287 A * | 9/2000 | Chen ............................... 433/24 |
| 6,120,289 A | 9/2000 | Cleary |
| 6,142,775 A | 11/2000 | Hansen et al. |
| 6,205,366 B1 | 3/2001 | Tang et al. |
| 6,217,324 B1 | 4/2001 | Kesling |
| 6,227,850 B1 | 5/2001 | Chishti et al. |
| 6,227,851 B1 | 5/2001 | Chishti et al. |
| 6,315,553 B1 * | 11/2001 | Sachdeva et al. ............... 433/24 |
| 6,350,120 B1 | 2/2002 | Sachdeva et al. |
| 6,471,511 B1 | 10/2002 | Chishti et al. |

(Continued)

FOREIGN PATENT DOCUMENTS

WO    WO 00/19931    4/2000

OTHER PUBLICATIONS

C.E. Seeley et al., "Response Surfacae Approximation of Non-Axisymmetric Features for Efficient Mechanical Analysis," GE Research & Development Center, Technical Information Series, 2000CRD013, Jul. 2000, 15 pages.

(Continued)

*Primary Examiner* — Cris L Rodriguez
*Assistant Examiner* — Heidi M Eide (57) ABSTRACT

Methods and apparatus for orthodontic treatment planning that involve determining an initial position of an orthodontic structure, determining an altered position, and generating response surface data using a mathematical relationship between the positions. The mathematical relationship may be defined by a number of parameters useful for determining one or more of the stress, strain, force, and moment associated with movement of the orthodontic structure. The mathematical relationship between the initial position and the altered position may be defined using a finite element analysis, empirically determined, or using other computational methodologies such as a finite difference methodology. The mathematical relationship may also be defined using an analytical methodology, such as elasticity and/or plasticity methodologies. Response surface data may be generated as a teaching aid, treatment planning aid, table, or other useful form, which may be useful, for example, for designing an orthodontic appliance, verifying an orthodontic prescription, and/or planning the prescription.

30 Claims, 6 Drawing Sheets

U.S. PATENT DOCUMENTS

| | | |
|---|---|---|
| 6,648,640 B2 | 11/2003 | Rubbert et al. |
| 6,739,870 B2 | 5/2004 | Lai et al. |
| 2001/0002310 A1 | 5/2001 | Chishti et al. |
| 2003/0059736 A1 | 3/2003 | Lai et al. |
| 2004/0161722 A1 | 8/2004 | Lai et al. |
| 2006/0073436 A1* | 4/2006 | Raby et al. .................. 433/24 |
| 2006/0147872 A1* | 7/2006 | Andreiko .................... 433/24 |

OTHER PUBLICATIONS

Dr. Akira Todoroki, "Teach Yourself Response Surface Methodology," Tokyo Institute of Technology, Department of Mechano-aerospace Engineering, date unknown, 4 pages.

C. Bouravel, et al., "Simulation of Orthodontic Tooth Movements," Journal of Orofacial Orthopedics, 1999.

J. Middleton, et al., "The Role of the Periodontal Ligament in Bone Modeling: The Initial Development of a Time-Dependent Finite Element Model," Amer. Jour. of Orthod. Dentof. Orthop., Feb. 1996, pp. 155-162.

Orthodontic Perspectives "Clarity Bracket Development"—A Technical Perspective by Jim Hansen, Spring 1997, vol. IV No. 1.

Ghosh, et al., Ceramic bracket design: An analysis using the finite element method. American Journal of Orthodontic and Dentofacial Orthopedics, Dec. 1995, pp. 575-582; Copyright © 1995 by the American Association of Orthodontists.

* cited by examiner

RESPONSE SURFACES FOR ORTHODONTIC TREATMENT PLANNING

FIELD OF THE INVENTION

The present invention relates to orthodontic treatment planning methods and, more particularly, to devices and methods for determining tooth movement and orthodontic prescriptions using response surfaces.

BACKGROUND

Orthodontics is a branch of dentistry that involves the movement of malpositioned teeth to orthodontically correct positions. Before prescribing an orthodontic treatment, X-rays and photographs of the patient's teeth and jaw structure are typically taken. Also, a mold of the patient's teeth is typically made. This mold, along with the X-rays and photographs, provide a model of the positions of the patient's teeth and dental arches prior to treatment.

The orthodontist also relies on a post treatment model of the altered positions of the patient's teeth and dental arches. This post-treatment model has typically been a mental model formulated in the mind of the orthodontist based on the orthodontist's experience and skill. However, computer programs are also known to assist the orthodontist in the development of a computerized post-treatment model. The orthodontist then devises an initial treatment strategy to move the patient's teeth and/or dental arches from their positions as represented by the pre-treatment model to the altered positions as represented by the post-treatment model, sometimes using interim steps to arrive at the ultimate position.

In order to implement the initial treatment strategy, the orthodontist applies various orthodontic appliances to the patient's teeth. In a typical treatment, brackets are attached to anterior, cuspid, bicuspid, and molar teeth. An arch wire is then held to the brackets by ligatures, so that the arch wire forms a track to guide movement of the brackets and the associated teeth to desired positions for correct occlusion. The brackets, arch wires, ligatures, and other ancillary devices used in correctly positioning teeth are commonly referred to as "braces".

The orthodontist's treatment strategy may require correction of the relative alignment between the upper and lower dental arches. For example, certain patients have a condition referred to as a Class II malocclusion in which the lower dental arch is located an excessive distance in a rearward direction relative to the location of the upper dental arch when the jaws are closed. Other patients may have an opposite condition referred to as a Class III malocclusion in which the lower dental arch is located in a forward direction of its desired location relative to the position of the upper dental arch when the jaws are closed.

Orthodontic treatment of Class II and Class III malocclusions are commonly corrected by movement of the upper and lower dental arches as units relative to one another. To this end, forces are often applied to each dental arch as a unit by applying a force to the brackets, the arch wires, and/or ancillary devices applied to the dental arch. In this manner, a Class II or Class III malocclusion can be corrected at the same time that the arch wires and the brackets are used to move individual teeth to desired positions relative to each other.

Corrections of Class II and Class III malocclusions are sometimes carried out by use of other devices such as headgear that includes strapping extending around the rear of the patient's head. The strapping is often coupled by tension springs to the brackets, arch wires, and/or ancillary devices. For correction of Class III malocclusions, the strapping can be connected by tension springs to a chin cup that externally engages the patient's chin. In either instance, the strapping and springs serve to apply a rearward force to the associated jaw.

Instead of using headgear, which is often considered unsatisfactory because it is visibly apparent, many practitioners and patients favour the use of intra-oral devices for correcting Class II and Class III malocclusions. Such devices are often located near the cuspid, bicuspid, and molar teeth and away from the patient's anterior teeth. As a result, intra-oral devices for correcting Class II and Class III malocclusions are hidden in substantial part once installed.

Orthodontic force modules made of an elastomeric material have also been used to treat Class II and Class III malocclusions. Pairs of such force modules are coupled between the dental arches on opposite sides of the oral cavity. Elastomeric force modules may be used in tension to pull the jaws together in a direction along reference lines that extend between the points of attachment of each force module. Such force modules may be O-rings or chain-type modules each made of a number of integrally connected O-rings. These modules are typically removable by the patient for replacement when necessary, since the module may break or the elastomeric material may degrade during use to such an extent that the amount of tension exerted is not sufficient. Non-removable intra-oral devices are also known which rely on flexible members that are connected to upper and lower dental arches of a patient. Moreover, telescoping tube assemblies may be used to urge the dental arches toward positions of improved alignment.

There are a wide variety of orthodontic appliances that are available to an orthodontist in the implementation of a treatment strategy. However, few tools exist to assist the orthodontist in the accurate selection of appliances that are likely to effectively implement the orthodontist's initial treatment strategy. Moreover, few tools exist to allow the orthodontist to accurately predict the effectiveness of the initial treatment strategy. Therefore, the treatment strategy is frequently modified over time as the orthodontist observes the actual movement of the teeth and dental arches in response to the orthodontist's treatment strategy.

SUMMARY OF THE INVENTION

The present invention is directed to methods and apparatus for orthodontic treatment planning. Embodiments of the present invention include those that employ methods for determining tooth movement and orthodontic prescriptions using response surfaces. According to one embodiment, a numerical method for determining movement of an orthodontic structure involves determining an initial position of an orthodontic structure, determining an altered position of the orthodontic structure, and generating response surface data using a mathematical relationship between the initial position and the altered position. The mathematical relationship may be defined by a number of parameters useful for determining one or more of the stress, strain, force, moment, movement rate, or other desirable parameter associated with movement of the orthodontic structure from the initial position to the altered position. The mathematical relationship between the initial position and the altered position may be defined using a finite element analysis, may be empirically determined, or may be defined using other computational methodologies such as a finite difference methodology. The mathematical relationship may also be defined using an analytical methodology, such as elasticity and/or plasticity methodologies or experimental measurement.

The response surface data may be generated as a teaching aid, a treatment planning aid, a table, or other useful form. Embodiments of methods in accordance with the present invention may further involve designing an orthodontic appliance using the generated response surface data. In other embodiments, methods may involve using the generated response surface data to select an appliance suitable for effecting movement of the orthodontic structure from the initial position to the altered position.

Other embodiments in accordance with the present invention are directed to orthodontic treatment planning methods involving determining first positions of a patient's teeth, determining desired second positions of the patient's teeth, selecting one or more response surfaces based on the determined first and second positions of the patient's teeth, and prescribing one or more orthodontic appliances based on the one or more response surfaces, the one or more response surfaces indicating that the prescription is acceptable. The response surface may be determined empirically, or may be determined using a numerical method, such as finite element analysis, finite difference, experimental measurement and/or an analytical methodology. The response surface may be provided as a look-up table, a graph, and/or an analytical expression.

Devices in accordance with the present invention are directed to systems for determining tooth movement including a means for determining an initial position of a tooth, a means for determining a desired position of the tooth, and a means for generating and/or using response surface data using a mathematical relationship between the initial position and the desired position.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

While the invention is amenable to various modifications and alternative forms, specifics thereof have been shown by way of example in the drawings and will be described in detail. It is to be understood, however, that the intention is not to limit the invention to the particular embodiments described. On the contrary, the intention is to cover all modifications, equivalents, and alternatives falling within the scope of the invention as defined by the appended claims.

DETAILED DESCRIPTION OF VARIOUS EMBODIMENTS

In the following description of the illustrated embodiments, reference is made to the accompanying drawings, which form a part hereof, and in which is shown by way of illustration, various embodiments in which the invention may be practiced. It is to be understood that the embodiments may be utilized and structural changes may be made without departing from the scope of the present invention.

The present invention relates to orthodontic treatment planning methods and devices. More particularly, the present invention relates to using response surfaces for orthodontic treatment planning, and/or appliance selection, and/or prescription validation. A response surface is a two or more dimensional output defined as a function of input parameters. For example, a mathematical relationship may define output parameters as a function of input parameters. A response surface may use the mathematical relationship to express the output in the form of data, graph, table, computed numerical output value, or other useful output.

An example of a response surface in accordance with the present invention provides anatomical stress and/or strain experienced by a patient as a result of a prescribed motion of one or more orthodontic structures, such as a patient's tooth. According to another embodiment of a response surface useful in accordance with the present invention, the response surface may be used to determine one or more of the stress, strain, force, and moment associated with movement of the orthodontic structure from its initial position to a desired position, such as an interim position or a final orthodontically correct position.

The response surface may include associated information, such as possible pain thresholds corresponding to levels of stress or strain, for example. A response surface may be a two-dimensional output of periodontic ligament structure (PDL) stress versus tooth movement magnitude, determined from any number of input variables. It is intended that the use of the term surface is not limited to a two-dimensional or three-dimensional surface. The surface may have any number of dimensions corresponding to any number of parameters or factors. Continuing with the pain example, a stress threshold may be established. Above the threshold stress, the pain experienced by the patient may be undesirable, indicating that a change to the prescription for that particular motion may be prudent.

Other examples of response surfaces in accordance with the present invention include data that describes the force on a tooth root, the maximum stress in a wire or bracket, or other desired output as a function of predetermined input parameters. For example, the input parameters may be six vectors that define the three dimensional movements and three rotational movements of a tooth between a first and second position, designated a prescribed movement input. In another example, the input parameters may be six vectors that define the three dimensional forces and three rotational forces applied to a tooth by one or a family of appliances, designated a prescribed force input.

Response surface data may be generated using a mathematical relationship between the initial position and the desired position of an orthodontic structure. For example, the mathematical relationship may be a polynomial equation having any number of terms and cross-terms. In a further example, the mathematical relationship may include a calculation of stresses on the orthodontic structure using empirical measurements from strain-gages on actual or modeled structures. Determination of stress and strain of orthodontic structures using finite element analysis is further described in commonly assigned U.S. Pat. No. 6,739,870, and US Patent Application Serial Number 2004/0161722, which are hereby incorporated herein by reference.

Figure 1A:
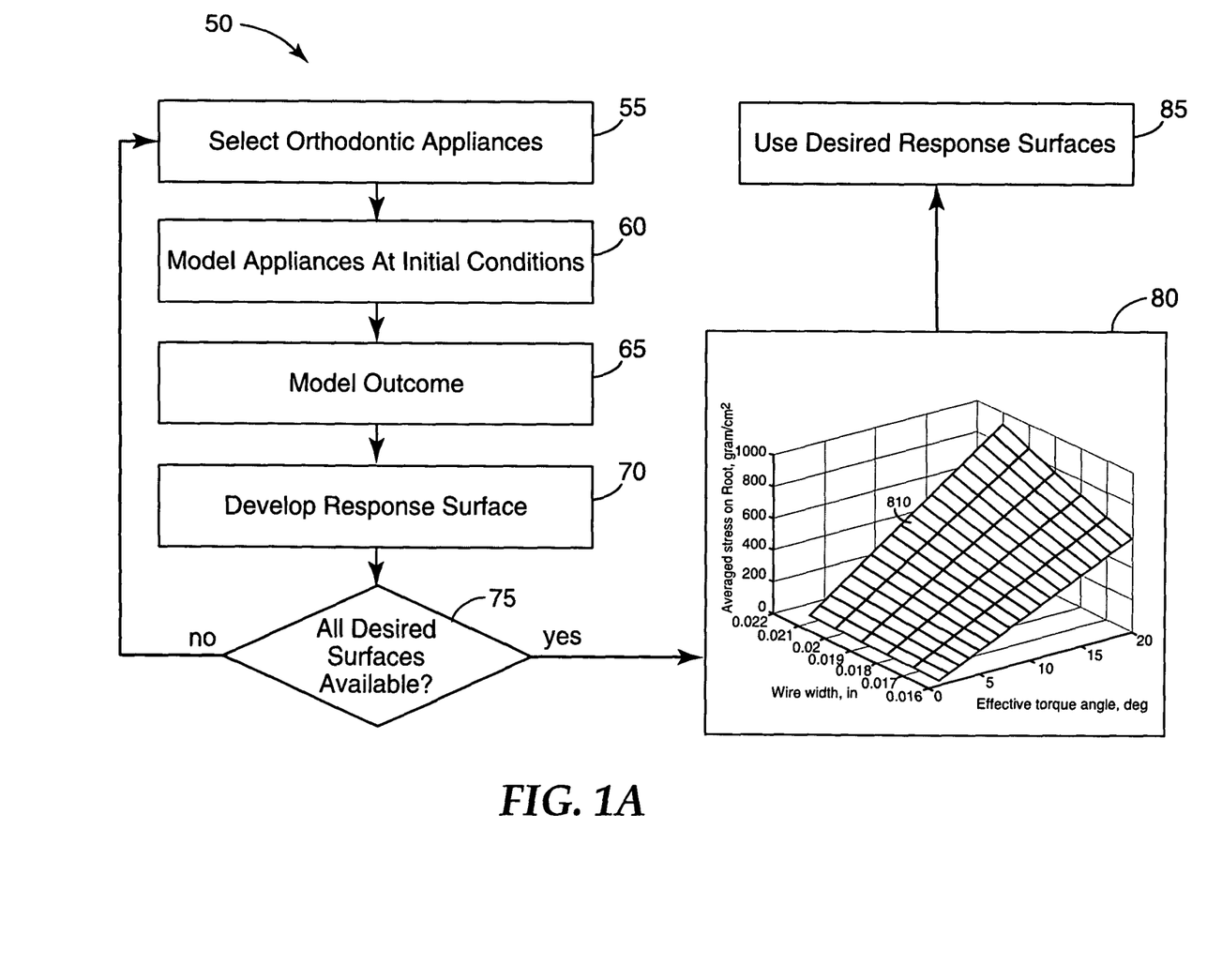
FIG. 1A illustrates a method for developing response surfaces and using the response surfaces in accordance with embodiments of the present invention.

FIG. 1A illustrates a method 50 for developing response surfaces and using the response surfaces in accordance with embodiments of the present invention. The response surfaces, such as a response surface 80, provide the advantages of using numerical methods of stress analysis to orthodontic procedure planning and appliance selection/validation, without the need for an orthodontist to have to perform the analyses for each patient. This allows the orthodontist to take advantage of the computational power associated with numerical methods, without having to learn methods such as FEA, and without the need for a computational platform such as a computer aided design (CAD) and/or computer aided engineering (CAE) system. Typically, a tooth is most influenced by the neighboring adjacent teeth through the archwire. The sphere of influence is diminished the further away an element is from a particular tooth. Each tooth may have its own response surface as a function of hardware used. For example, the coordinate axis may be representative of the x-y planer motion of the teeth, and the response may be either stress or strain.

The orthodontist may be provided with the response surfaces by a manufacturer of the appliances, or by an organization that performs numerical methods, for example. In order to improve clarity, and as a non-limiting example, a manufacturer providing the response surfaces to an orthodontist will be used while referring to FIG. 1A for discussion purposes only. The manufacturer selects 55 orthodontic appliances for modeling. The manufacturer of appliances may choose to provide a set of response surfaces for each appliance type manufactured. For example, arch wires, tooth brackets, and ligatures may be modeled numerically, empirically or analytically.

The appliances are then modeled at initial conditions 60, and the model is analyzed 65 using a numerical method, which provides an outcome of the model. Modeling of orthodontic hardware typically includes implicit properties of the hardware, teeth, and potting material. Initial tooth coordinates and the desired displacement of each and every tooth typically represents the input or known parameters. The resulting outcome of the tooth movement to the final position or some intermediate position provides a predicted root stress.

The outcome of the model is then used to create 70 the response surface for the parameters used in that particular model. For example, a set of braces may be modeled along with teeth, gums, and jawbone, with the teeth at an orthodontically correct arrangement. Parameters may then be varied, and one or more response surfaces created that represent the response to the variation(s). As a non-limiting specific example, teeth displacement may be prescribed that may be useful to correct a type II malocclusion to the orthodontically correct arrangement. A response surface may be provided that determines rate of movement for the teeth as a function of arch wire diameter. Patient age may be an important factor, for example. It may be desirable to create a response surface that determines rate of movement for the teeth as a function of arch wire diameter for each age group. As new factors are determined, response surfaces may be determined for each factor, group of factors, and cross-factor.

If all the desired surfaces have not been created at a decision 75, then other parameters are used and/or other appliances are selected, and steps 55, 60, 65, and 70 are repeated for the new parameters. After all desired response surfaces have been created, the response surfaces 80 are provided to a user, such as an orthodontist, to use 85 the desired response surfaces for decision-making. For example, one use 85 is a method 300, which will be described in greater detail with reference to FIG. 3 below.

Figure 1B:
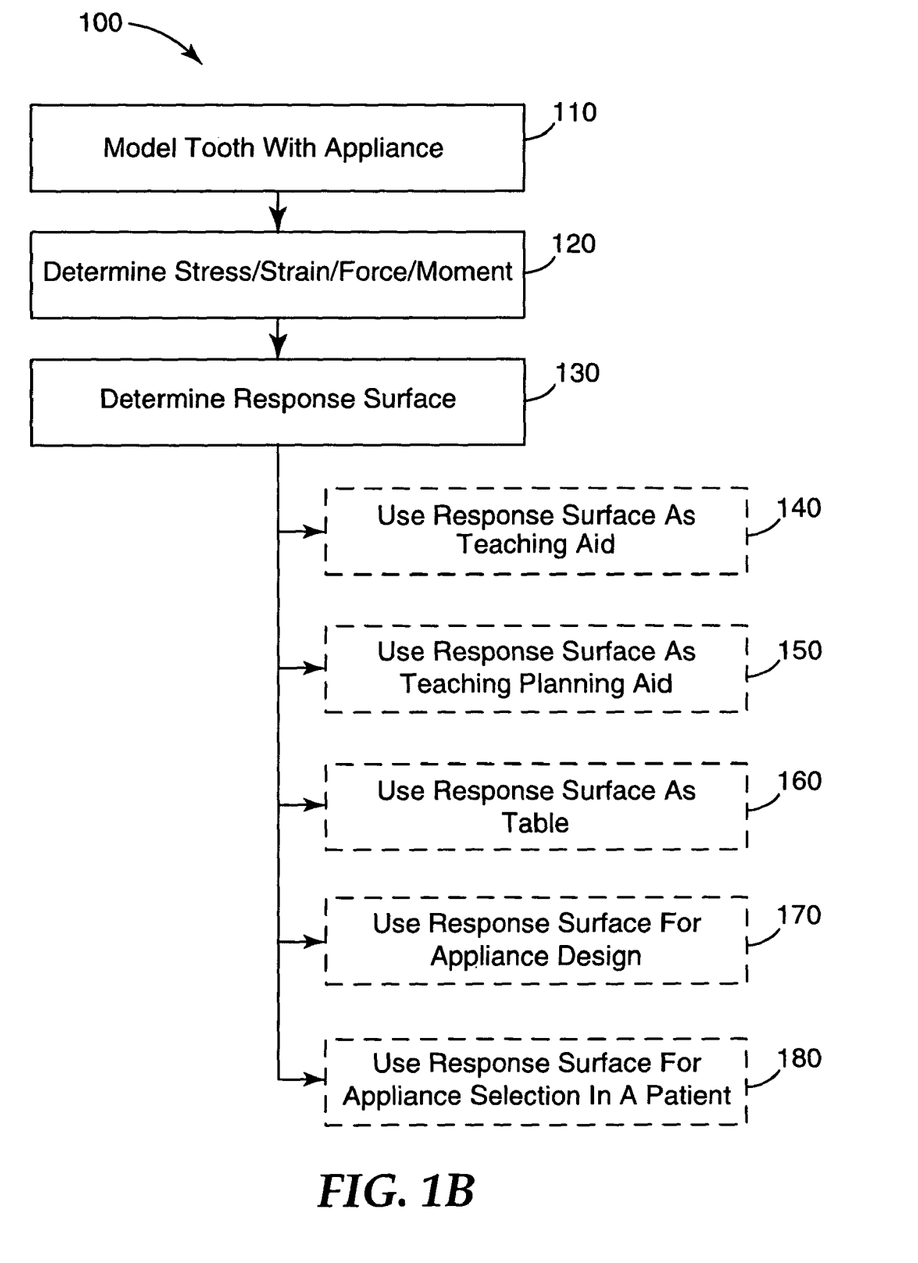
FIG. 1B illustrates a method for determining a response surface associated with the movement of a tooth during an orthodontic procedure in accordance with the present invention.

FIG. 1B illustrates a method 100 for determining a response surface associated with the movement of a tooth during an orthodontic procedure. Each orthodontic appliance and/or family of appliance type and/or grouping of appliances may be associated with one or more response surfaces useful in accordance with the present invention. The embodiment illustrated in FIG. 1B models 110 one such appliance or family of appliances, such as by creating a three dimensional solid model in a CAD/CAE workstation. The model may then be analyzed 120, such as by using numerical methods, to determine one or more response surfaces 130. A family of response surfaces may be generated using the method 100, such that the output of the response surface, tooth root stress for example, may be easily determined for a prescribed orthodontic structure undergoing a prescribed displacement. The response surfaces may be generated independently of the specific patient and/or specific prescription, thereby reducing the need for complex modeling and computation capabilities at an orthodontist's office, for example.

The response surfaces 130 may be useful for a variety of applications in accordance with the present invention. The response surface data may be generated as a teaching aid 140, a treatment planning aid 150, a table 160 (e.g. a look-up table, either provided as numerical data stored in a memory, or as a print-out), or other useful form. The table 160 may be incorporated into a database where digital movement of images of teeth with a known displacement vector can interpolate desired stress, force, strain, or other parameter from associated tabulated displacement.

Embodiments of methods in accordance with the method 100 may further involve designing 170 an orthodontic appliance using the generated response surface data. In other embodiments, methods may involve using the generated response surface data to select an appliance suitable 180 for effecting movement of the orthodontic structure from the initial position to the desired position.

It may be useful in other embodiments in accordance with the present invention to provide patient specific information as an input to a system for generating response surfaces, in order to develop one or more patient specific response surfaces. Examples of patient specific input include, but are not limited to: tetracycline staining of patient teeth, patient age, patient disease state for gum disease, patient pain tolerance level, compromised patient health attributes, or other patient related information where patient specific response surfaces are desired.

It may be desirable, in further embodiments, to provide interim patient movement information as input parameters for response surface generation. For example, a patient may be at an interim treatment stage, and a particular prescription may not be producing expected results. The patient's interim teeth positions may be modeled, and provided as feedback into the response surface generation system along with current prescription information. An analysis may be run on the response surface generation system, and material properties and/or other parameters may be adjusted such that a new set of response surfaces are provided that are consistent with the patient results at the interim positions. The revised response surfaces may then be used to generate a new prescription for the individual patient that more accurately reflects results of particular appliances in that patient.

Figure 2:
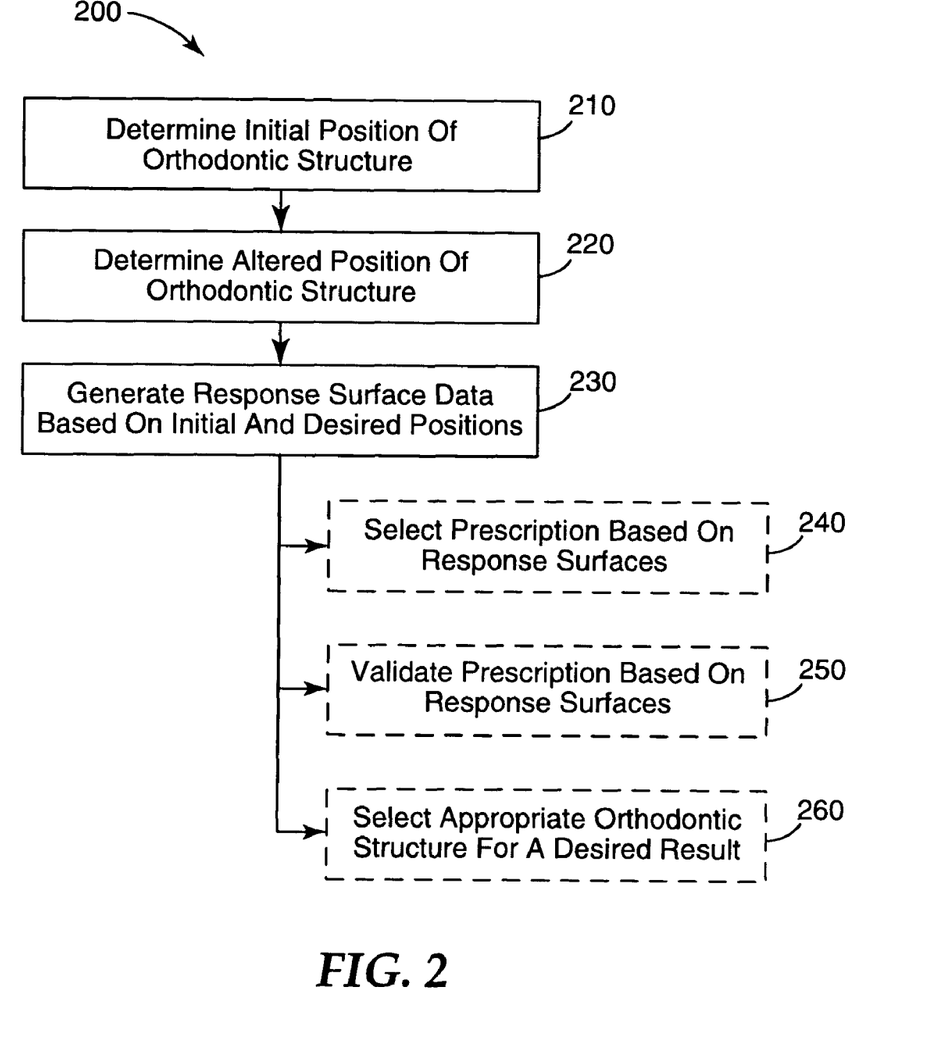
FIG. 2 illustrates a method for determining movement of an orthodontic structure in accordance with embodiments of the present invention.

FIG. 2 illustrates a method 200 for determining movement of an orthodontic structure in accordance with embodiments of the present invention, including, for example, methods for determining tooth movement and orthodontic prescriptions using response surfaces. According to the embodiment illustrated in FIG. 2, a numerical method 200 for determining movement of an orthodontic structure involves determining an initial position of an orthodontic structure 210, determining a desired position of the orthodontic structure 220, and generating response surface data 230 using a mathematical relationship between the initial position and the desired position.

The mathematical relationship may be defined by a number of parameters useful for determining one or more of the stress, strain, force, moment, rate of motion, pain, or other useful output associated with movement of the orthodontic structure from the initial position to the desired position. As described earlier, the mathematical relationship between the initial position and the desired position may be defined using numerical methods, may be empirically determined, or may be defined using other computational methodologies such as a finite difference methodology. The mathematical relationship may also be defined using an analytical methodology, such as elasticity and/or plasticity methodologies.

Embodiments of methods in accordance with the method 200 may further involve selecting a prescription 240 based on the response surface data 230. In other embodiments, methods may involve using the generated response surface data to validate 250 a proposed prescription, or select an appropriate orthodontic structure 260 for a desired result. For example, a response surface may provide the maximum stress of a wire used to link several brackets. A wire diameter may be selected based on the response surface data.

Figure 3:
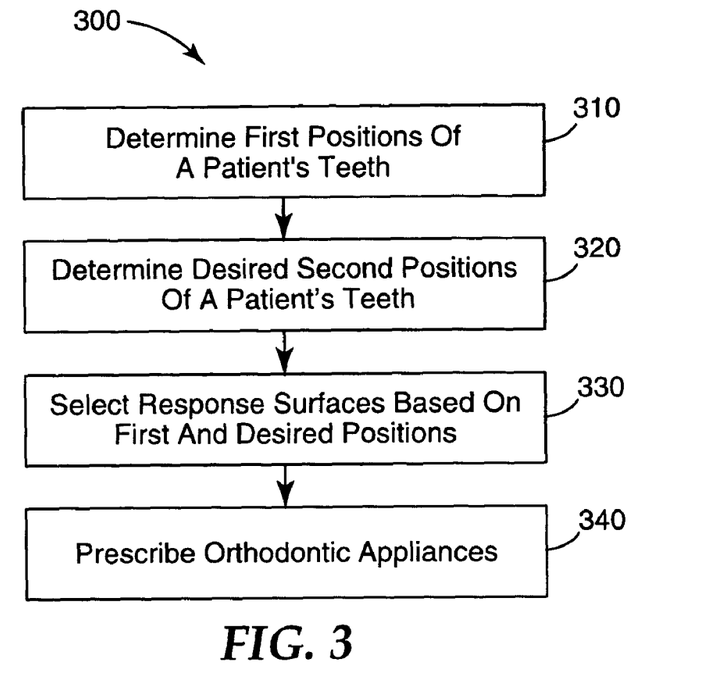
FIG. 3 illustrates a method for orthodontic treatment planning in accordance with embodiments of the present invention.

FIG. 3 illustrates a method 300 for orthodontic treatment planning in accordance with embodiments of the present invention. An orthodontic treatment planning method 300 involves determining 310 first positions of a patient's teeth, determining 320 desired second positions of the patient's teeth, selecting 330 one or more response surfaces based on the determined first and second positions of the patient's teeth, and prescribing 340 one or more orthodontic appliances based on the one or more response surfaces, the one or more response surfaces indicating that the prescription is acceptable.

Determining 310 the first positions of the patient's teeth may be done, for example, by molding the patient's teeth, and measuring the positions. The mold may be used to produce a plaster-cast model of the patient's teeth, and the plaster-cast model may be digitized to provide a three-dimensional surface model. Digitization may be performed using known methods, such as by using a computerized numerical control system, or other digitization methodology. Another method for measuring the patient's teeth involves the orthodontist's use of a caliper or other measurement tool to simply determine the displacements of a particular tooth or set of teeth from a desired position.

Once the initial positions are determined, and modeled in a CAD/CAE system, for example, the teeth may be manipulated using the CAD/CAE system, and placed into desired final positions. For example, each tooth for a patient may be modeled as a three-dimensional virtual solid in the CAD/CAE system. The CAD/CAE system may then be used to perform a virtual manipulation of the three-dimensional virtual solids. The CAD/CAE operator may rotate and displace each virtual tooth until an orthodontically correct positioning is reached. Alternately, the CAD/CAE system may be programmed to recognize an orthodontically correct arrangement, and perform the virtual manipulations automatically.

If the desired final positions include large displacements from the initial positions, the movement may be divided into several smaller incremental movements. The displacement to the incremental or final position, determined by the CAD model (or other imaging or measurement techniques) may then be referenced to the appropriate response surface equations or tables to determine the stresses, for example, on the teeth associated with the movement of the teeth from the first to desired positions. Response surface look-up tables may then be used to decide which appliances are appropriate for the prescribed motion.

Figure 4:
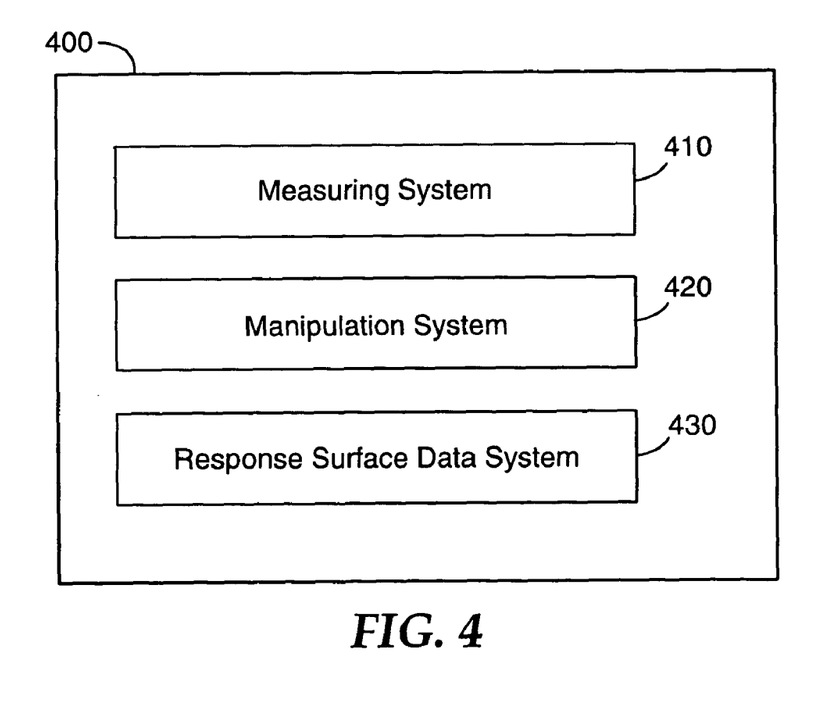
FIG. 4 is a block diagram of a system configured to provide response surfaces and/or use response surfaces for orthodontic treatment planning in accordance with embodiments of the present invention.

FIG. 4 is a block diagram of a system 400 configured to provide response surfaces and/or use response surfaces for orthodontic treatment planning in accordance with embodiments of the present invention. The system 400 is configured to implement the method 300 described above, as one example of systems in accordance with the present invention. The system 400 includes a measuring system 410 for determining an initial position of one or more teeth and/or appliances. Suitable examples of measuring system 410 include the CNC system described with reference to FIG. 3, calipers, and measurements obtainable from X-rays, CT scans, MRI scans, and other measurement methodologies.

A manipulation system 420 is used to determining a desired position of the one or more teeth and/or appliances. Suitable examples of manipulation system 420 include the CAD/CAE workstation as described with reference to FIG. 3, a physical model instrumented for positional determinations, and a listing by an orthodontist of the displacements needed to bring a tooth from its current position to the desired position.

A response surface data system 430 uses a mathematical relationship between the initial position and the desired position to generate response surfaces in accordance with the present invention. The response surface system 430 may generate the response surfaces as part of the system 400, or the response surfaces may be provided as a data set to the response surface system 430 in an alternate embodiment. A suitable response surface data generating system 430 is a workstation running FEA software, as described with reference to FIG. 1B, or may be implemented in software, firmware, hardware, or some combination without departing from the scope of the present invention.

The components, functionality, and configurations described above and/or depicted in FIG. 4 are intended to provide an understanding of various features and combinations of features that may be incorporated in an orthodontic treatment planning system in accordance with embodiments of the present invention. It is understood that a wide variety of device configurations are contemplated, ranging from relatively sophisticated to relatively simple designs. Illustrated in FIG. 4 is a processor-based response surface system 430 which may include a microprocessor coupled to appropriate memory (volatile and/or non-volatile), it being understood that any logic-based control architecture may be used.

Figure 5:
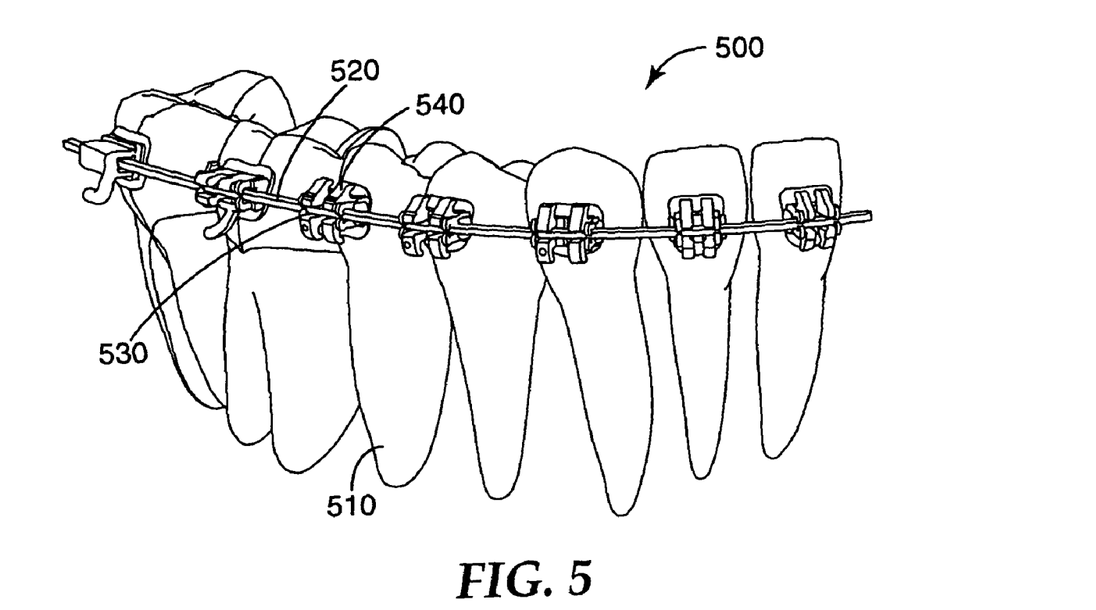
FIG. 5 illustrates a specific example embodiment of an orthodontic arrangement in accordance with the present invention.

FIG. 5 illustrates a specific example embodiment of an orthodontic arrangement 500 in accordance with the present invention. It is known that a mal-inclined tooth 510 may be subjected to torque from an arch wire 520 when a rectangular arch wire is placed into a wire slot 530 of an orthodontic bracket 540 bonded to the tooth 510. Torque generated by the arch wire 520 can be calculated based on the wire geometry, wire material property, bracket arch wire slot 520 width and inter-bracket distance.

Figure 6:
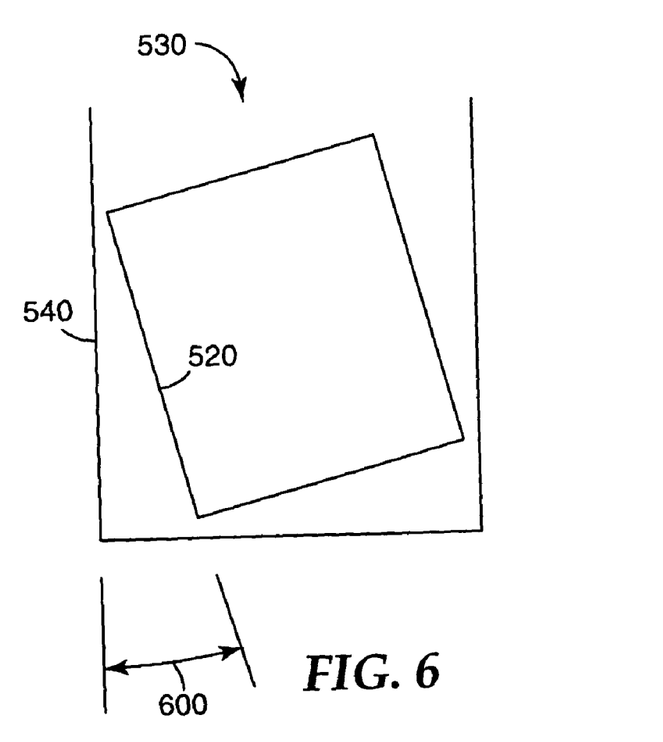
FIG. 6 is a graph illustrating the cross-section of a rectangular wire and wire slot.

FIG. 6 is a graph illustrating the cross-section of rectangular arch wire 520 and wire slot 530. The arch wire 520 delivers a torque on the arch wire slot 530 and in turn on the tooth that the bracket is bonded on. The arch wire 520 is illustrated as having a width b and a height h. The torque is generated when the arch wire 520 is twisted (not shown) due to the mal-inclination of the tooth minus a torque loss angle 600 from the clearance between the arch wire 520 and arch wire slot size 530.

As shown in FIGS. 5 and 6, the root of the tooth 510 can move gingivally toward the mouth. Stress and strain fields are generated on the root of the tooth 510, periodontal ligament between the tooth 510 and alveolar bone and alveolar bond itself. The stress and strain fields are responsible for the tooth 510 movement that the orthodontist is trying to manage. Appropriate stress and strain levels will accelerate the tooth 510 movement and reduce patient discomfort during the orthodontic treatment. Excessive stress/strain will generate trauma to the patient's tissue and slow down the tooth 510 movement. High stress/strain will have other problems such as root resorption. Stress too low will not move the teeth effectively.

Figure 7:
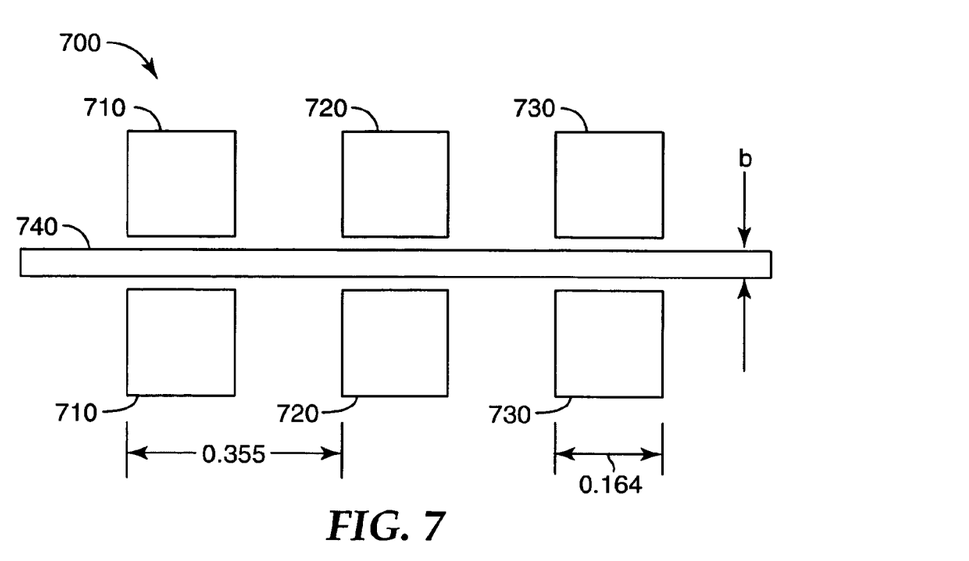
FIG. 7 is a block diagram illustrating the torque on a middle tooth of a 3-bracket system when the middle bracket is subject to torque from the arch wire.

Referring now to FIG. 7, it will be convenient for an orthodontist to obtain stress/strain information on the root if the response surfaces are generated to relate the tooth mal-inclination angle and arch wire size to the stress level on the root of the tooth. For example, consider the torque on a middle tooth of a 3-bracket system 700 when the middle bracket is subject to torque from the arch wire as illustrated in FIG. 7. The 3-bracket system 700 includes a first bracket 710, a second bracket 720, a third bracket 730, and an arch wire 740 having a width b. The arch wire 740 runs through a slot in each bracket 710, 720, 730. As a specific example, the brackets 710, 720, 730 are illustrated in FIG. 7 as 0.164 inches (0.42 cm) mesial-distal dimension, with a bracket distance (L) of 0.355 inches (0.90 cm).

The torque is related to the effective torque angle $\phi$ ($\phi$=Tooth mal-inclination angle−Torque loss angle due to the wire and wire slot clearance) of the twisted wire due to the mal-inclined tooth at the middle bracket with a length (L) in the wire as in the following equation 1:

$$T = \frac{\phi GJ}{2L}$$ (Equation 1)

where G is shear modulus of the wire material and J is the polar moment of inertial that can be calculated as follows using Equation 2:

$$J = \frac{bh(b^2 + h^2)}{12}$$ (Equation 2)

Assuming that the moment arm, m, from the bracket to the center of resistance on the root that will resist the torque and the average root surface is A, the average stress, S, can be related to the torque as in Equation 3:

$$S = \frac{T}{2mA}$$ (Equation 3)

From Equations 1, 2 and 3, the average stress on the root can be calculated as:

$$S = \frac{\phi GJ}{mAL} = \frac{\phi G}{mAL} \frac{bh(b^2 + h^2)}{12}$$ (Equation 4)

As a specific numerical example, response surfaces can be built from Equation 4 to relate the stress to the twisted wire angle, the wire width, b with the following values:
G=8.08×10$^8$ gram/cm$^2$ (Shear modulus for steel)
m=0.95 cm (Moment arm from bracket to center resistance of tooth)
A=0.7 cm$^2$ (Projected labiolingual area of root)
L=0.90 cm (Bracket distance)
$\phi$=1 to 11 degrees (Effective wire torque angles of interest)
w=0.022" (Wire slot width)
h=0.025" (0.064 cm) (Arch wire height)
b=0.016", 0.017", 0.018", 0.019", 0.020" and 0.021" (Typical commercially available arch wire widths)

Using Equation 4, the averaged stress on the root can be calculated and tabulated as illustrated in Table 1.

TABLE 1

Tabulated Torque Angle and Stress for Various Wire Sizes.

| Effective torque angle | | S, average stress, gram/cm^2 under different wire widths | | | | | |
|---|---|---|---|---|---|---|---|
| deg | rad | 0.016 | 0.017 | 0.018 | 0.019 | 0.02 | 0.021 |
| 1 | 0.017 | 28.8 | 31.7 | 34.8 | 38.2 | 41.8 | 45.7 |
| 2 | 0.035 | 57.5 | 63.4 | 69.7 | 76.4 | 83.6 | 91.3 |
| 3 | 0.052 | 86.3 | 95.1 | 104.5 | 114.6 | 125.4 | 137.0 |
| 4 | 0.070 | 115.0 | 126.8 | 139.4 | 152.9 | 167.3 | 182.7 |
| 5 | 0.087 | 143.8 | 158.5 | 174.2 | 191.1 | 209.1 | 228.3 |
| 6 | 0.105 | 172.5 | 190.2 | 209.1 | 229.3 | 250.9 | 274.0 |
| 7 | 0.122 | 201.3 | 221.9 | 243.9 | 267.5 | 292.7 | 319.6 |
| 8 | 0.140 | 230.0 | 253.6 | 278.8 | 305.7 | 334.5 | 365.3 |
| 9 | 0.157 | 258.8 | 285.3 | 313.6 | 343.9 | 376.3 | 411.0 |
| 10 | 0.175 | 287.5 | 316.9 | 348.4 | 382.1 | 418.2 | 456.6 |
| 11 | 0.192 | 316.3 | 348.6 | 383.3 | 420.4 | 460.0 | 502.3 |
| 12 | 0.209 | 345.0 | 380.3 | 418.1 | 458.6 | 501.8 | 548.0 |
| 13 | 0.227 | 373.8 | 412.0 | 453.0 | 496.8 | 543.6 | 593.6 |
| 14 | 0.244 | 402.5 | 443.7 | 487.8 | 535.0 | 585.4 | 639.3 |
| 15 | 0.262 | 431.3 | 475.4 | 522.7 | 573.2 | 627.2 | 684.9 |
| 16 | 0.279 | 460.0 | 507.1 | 557.5 | 611.4 | 669.1 | 730.6 |
| 17 | 0.297 | 488.8 | 538.8 | 592.3 | 649.6 | 710.9 | 776.3 |
| 18 | 0.314 | 517.6 | 570.5 | 627.2 | 687.8 | 752.7 | 821.9 |
| 19 | 0.332 | 546.3 | 602.2 | 662.0 | 726.1 | 794.5 | 867.6 |
| 20 | 0.349 | 575.1 | 633.9 | 696.9 | 764.3 | 836.3 | 913.3 |

Figure 8:
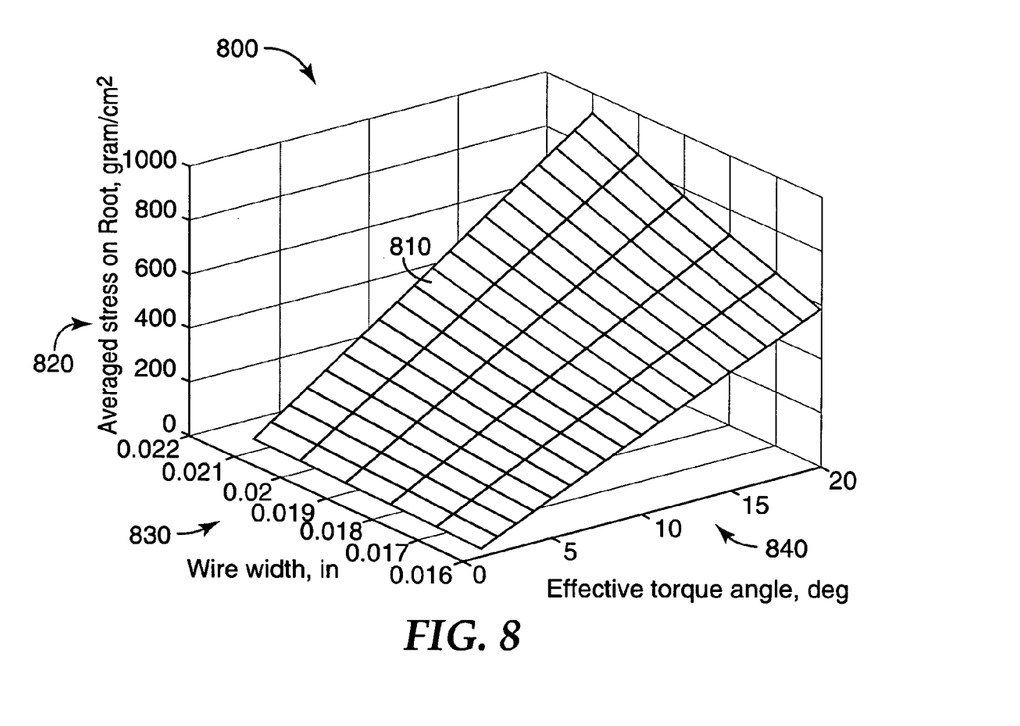
FIG. 8 is a specific example of a response surface in accordance with the present invention.

The data from Table 1 is plotted as a response surface 810 as illustrated in FIG. 8. In FIG. 8, a graph 800 plots average root stress 820 as a function of wire width 830 and effective torque angle 840. The response surface 810 may be used to quickly determine the average root stress 820 for a given wire width 830 and effective torque angle 840, without any further calculation or analysis required.

For example, if the middle tooth has a mal-inclined angle of 20°, torque loss angles for a 0.022" wire slot width and the effect torque angles, $\phi$, for different rectangle wire sizes, b×0.025" with a 0.003" (0.0076 cm) corner radius, are as seen in Table 2:

TABLE 2

Torque Loss and Effective Torque Angle for Various Wire Sizes.

| | b, in | | | | | |
| --- | --- | --- | --- | --- | --- | --- |
| b, cm | 0.016 0.0406 | 0.017 0.0432 | 0.018 0.0457 | 0.019 0.0483 | 0.02 0.0508 | 0.021 0.0533 |
| Torque loss, degrees | 22 | 18 | 15 | 11 | 7 | 4 |
| Effective torque angle, degrees | 0 | 2 | 5 | 9 | 13 | 16 |

Orthodontists can find the averaged stresses on the root using the response surface 610 or the look-up table for different wire sizes. The results are added to the table as is seen in Table 3 below:

TABLE 3

Torque Loss, Effective Angle, and Stress for Various Wire Sizes

| | b, in | | | | | |
| --- | --- | --- | --- | --- | --- | --- |
| b, cm | 0.016 0.0406 | 0.017 0.0432 | 0.018 0.0457 | 0.019 0.0483 | 0.02 0.0508 | 0.021 0.0533 |
| Torque loss, degrees | 22 | 18 | 15 | 11 | 7 | 4 |
| Effective torque angle, degrees | 0 | 2 | 5 | 9 | 13 | 16 |
| S, average stress | 0 | 63.4 | 174.2 | 343.9 | 543.6 | 730.6 |

Bioprogressive Therapy recommends 100-150 grams/cm$^2$ as the optimum stress on the root for tooth movement. For example, in this specific embodiment, 0.01"×0.025" may be chosen to be the right wire to deliver 174 grams/cm$^2$ according the above table.

The foregoing description of the various embodiments of the invention has been presented for the purposes of illustration and description. It is not intended to be exhaustive or to limit the invention to the precise form disclosed. Many modifications and variations are possible in light of the above teaching. It is intended that the scope of the invention be limited not by this detailed description, but rather by the claims appended hereto.

What is claimed is:

1. A numerical method for determining movement of an orthodontic structure, comprising:
   determining an initial position of an orthodontic structure;
   determining an altered position of the orthodontic structure; and
   generating response surface data representing a mathematical relationship between an output parameter and input parameters associated with movement of the orthodontic structure from the initial position to the altered position, the input parameters characterizing a class of patient types and including a variable parameter having a corresponding relationship with another one of the input parameters as defined by the response surface data, and the response surface data providing output parameters for different orthodontic prescriptions for different patients respectively in the class of patient types and, therein transforming the initial and altered position of the orthodontic structure, the variable parameter, and the mathematical relationship into different output parameters for different orthodontic prescriptions for different patients respectively in the class of patient types.

2. The method of claim 1, wherein the response surface data represents one or more of stress, strain, force, rate of motion, and moment associated with movement of the orthodontic structure from the initial position to the altered position, and wherein the response surface data is independent of any specific patient and rather applicable to a group of patients defined by the variable parameter.

3. The method of claim 1, wherein the response surface data is generated using a logic-based circuit, including a computer-based system, that performs a finite element analysis.

4. The method of claim 1, wherein the response surface data is generated empirically.

5. The method of claim 1, wherein the response surface data is generated using a logic-based circuit, including a computer-based system, that performs a finite difference methodology.

6. The method of claim 1, wherein the response surface data is generated using a logic-based circuit, including a computer-based system, that performs an analytical methodology.

7. The method of claim 1, wherein the response surface data is generated as a teaching aid.

8. The method of claim 1, wherein the response surface data is generated as a treatment planning aid.

9. The method of claim 1, wherein the response surface data is generated using a logic-based circuit, including a computer-based system, that provides the surface data as a table configured to aid in selection of an appliance for effecting movement of the orthodontic structure from the initial position to the altered position, for a patient in the class of patient types, responsive to setting the variable parameter to determine the other input parameter.

10. The method of claim 9, wherein the table is used to provide adjustment data useful to each of the orthodontic prescriptions.

11. The method of claim 1, further comprising designing an orthodontic appliance using the generated response surface data.

12. The method of claim 1, further comprising using the generated response surface data to select an appliance suitable for effecting movement of the orthodontic structure from the initial position to the altered position, for a patient in the class of patient types, by setting the variable parameter to determine another input parameter.

13. The method of claim 1, wherein the variable parameter is patient age, and wherein the response surface data is independent of any specific patient and rather applicable to a group of patients having said patient age.

14. An orthodontic treatment planning method, comprising:
   determining first positions of a patient's teeth;
   determining desired second positions of the patient's teeth;

using a logic-based circuit, including a computer-based system, for selecting one or more response surfaces based on the determined first and second positions of the patient's teeth, the one or more response surfaces representing one or more output parameters as a function of input parameters associated with movement of the patient's teeth, the input parameters characterizing a class of patient types and including a variable parameter having a corresponding relationship with another one of the input parameters as defined by the one of more response surfaces, and the one or more response surfaces providing output parameters for different orthodontic prescriptions for different patients respectively in the class of patient types; and prescribing one or more orthodontic appliances based on the one or more response surfaces, the one or more response surfaces indicating that the one or more orthodontic appliances is acceptable.

15. The method of claim 14, wherein at least one response surface is determined empirically.

16. The method of claim 14, wherein at least one response surface is determined using a numerical method.

17. The method of claim 16, wherein at least one response surface is determined using a finite element analysis.

18. The method of claim 16, wherein at least one response surface is determined using a finite difference methodology.

19. The method of claim 16, wherein at least one response surface is determined using an analytical methodology.

20. The method of claim 14, wherein at least one response surface is provided as a look-up table configured to aid in the step of prescribing the one or more orthodontic appliances responsive to setting the variable parameter to determine another input parameter.

21. The method of claim 20, wherein the look-up table is used to provide adjustment data useful to each of the orthodontic prescriptions.

22. The method of claim 14, wherein at least one response surface is provided as an analytical expression, wherein one of the input parameters is defined as a function of another input parameter.

23. The method of claim 14, wherein the one or more input parameters include one or more of patient age, patient teeth staining, patient pain tolerance, and patient gum disease state.

24. The method of claim 14, wherein the one or more output parameters include one or more of anatomical stress, anatomical strain, force, moment, rate of motion, and patient pain.

25. A non-transitory computer-readable medium having computer-executable instructions for executing a numerical method for determining tooth movement, the computer-executable instructions performing steps comprising:

determining an initial position of an orthodontic structure;
determining an altered position of the orthodontic structure;
generating response surface data representing a mathematical relationship between the initial position and the altered position, the mathematical relationship defined by a number of parameters useful for determining one or more of the stress, strain, force, and moment associated with movement of the orthodontic structure from the initial position to the altered position, the input parameters characterizing a class of patient types and including a variable parameter having a corresponding relationship with another one of the input parameters as defined by the response surface data, and the response surface data providing output parameters for different orthodontic prescriptions for different patients respectively in the class of patient types.

26. A system for determining tooth movement, comprising:

means for determining an initial position of a tooth;
means for determining an altered position of the tooth; and
means, including a computer-based system for generating response surface data by selecting one or more response surfaces representing a mathematical relationship between an output parameter and input parameters associated with movement of the tooth from the initial position and the altered position, the input parameters characterizing a class of patient types and including a variable parameter having a corresponding relationship with another one of the input parameters as defined by the one or more response surfaces, and the response surface data providing output parameters for different orthodontic prescriptions for different patients respectively in the class of patient types.

27. The system of claim 26, comprising means for selecting an appliance suitable for effecting movement of the tooth from the initial position to the altered position.

28. A numerical method for determining movement of an orthodontic structure, comprising:

determining an initial position of an orthodontic structure;
determining an altered position of the orthodontic structure; and
generating, using at least one of an analytical method, an empirical method and a mathematical method, response surface data representing a mathematical relationship between output parameters and input parameters associated with movement of the orthodontic structure from the initial position to the altered position, the input parameters characterizing a class of patient types and including a variable parameter having a corresponding relationship with another one of the input parameters as defined by the response surface data, and, therein transforming the initial and altered position of the orthodontic structure, the variable parameter, and the mathematical relationship into different output parameters for different orthodontic prescriptions for different patients respectively in the class of patient types.

29. The method of claim 28, further including using a logic-based means for the step of generating the response surface data.

30. The method of claim 29, wherein the logic-based means is a programmed computer.

* * * * *

UNITED STATES PATENT AND TRADEMARK OFFICE
CERTIFICATE OF CORRECTION

PATENT NO. : 7,972,134 B2
APPLICATION NO. : 11/096785
DATED : July 5, 2011
INVENTOR(S) : Ming-Lai Lai et al.

It is certified that error appears in the above-identified patent and that said Letters Patent is hereby corrected as shown below:

Column 12
Claim 3, Line 9, delete "fmite" and insert -- finite --, therefor.

Signed and Sealed this
Thirteenth Day of December, 2011

David J. Kappos
*Director of the United States Patent and Trademark Office*